US00PP24257P3

(12) United States Plant Patent
Mang

(10) Patent No.: US PP24,257 P3
(45) Date of Patent: Feb. 18, 2014

(54) **VARIETY OF *CALATHEA* PLANT NAMED 'PRINCESS JESSIE'**

(50) Latin Name: ***Calathea roseopicta* (Linden) Regel**
Varietal Denomination: Princess Jessie

(75) Inventor: Rui Mang, Almere (NL)

(73) Assignees: Siere Handel B.V., Almere (NL); Fernselect B.V., Aalsmeer (NL)

( * ) Notice: Subject to any disclaimer, the term of this patent is extended or adjusted under 35 U.S.C. 154(b) by 278 days.

(21) Appl. No.: 13/135,398

(22) Filed: Jul. 1, 2011

(65) Prior Publication Data

US 2013/0007934 P1 Jan. 3, 2013

(51) Int. Cl.
*A01H 5/00* (2006.01)

(52) U.S. Cl.
USPC ..... Plt./375

(58) Field of Classification Search
USPC ..... Plt./375
See application file for complete search history.

(56) References Cited

PUBLICATIONS

GTITM UPOVROM Citation for 'Princess Jessie' as per QZ PBR 20070679; Jun. 15, 2007.*

* cited by examiner

*Primary Examiner* — Kent L Bell
(74) *Attorney, Agent, or Firm* — The Webb Law Firm

(57) ABSTRACT

A new and distinct cultivar of *Calathea roseopicta* (Linden) Regel plant named 'Princess Jessie' having black leaves with a wide pink band on the leaf edges.

4 Drawing Sheets

Botanical classification: *Calathea roseopicta* (Linden) Regel.
Varietal denomination: 'Princess Jessie'.

BACKGROUND OF THE INVENTION

The present invention comprises a new and distinct cultivar of *calathea* botanically classified as *Calathea roseopicta* (Linden) Regel and known by the varietal name 'Princess Jessie'. The new variety was discovered and selected by the breeder in a cultivated environment in 2006 in Aalsmeer, The Netherlands as a naturally occurring mutation in a tissue culture plant population of unpatented and unnamed *Calathea roseopicta* plants. Subsequently, the new variety was asexually reproduced by tissue culture and cuttings in Dongguang, Republic of China in January of 2007.

The most similar *calathea* variety to 'Princess Jessie' known to the breeder is 'Dottie' (U.S. Plant Pat. No. 12,736). 'Princess Jessie' differs from 'Dottie' in that its upper leaf surfaces bear a much broader bright pink (between N66C and 67B) zone on the edge of the leaves. Also, the main color of the upper leaf surface of 'Princess Jessie' is black (202A), while the main color of the upper leaf surface of 'Dottie' is a very dark grey-green. Further, under growing conditions in The Netherlands, 'Dottie' has a more compact growth habit than 'Princess Jessie'. The following characteristics distinguish the new variety from other *calathea* varieties known to the breeder:

Black leaves;
Compact growth habit; and
Very wide pink band on the edge of the leaves.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
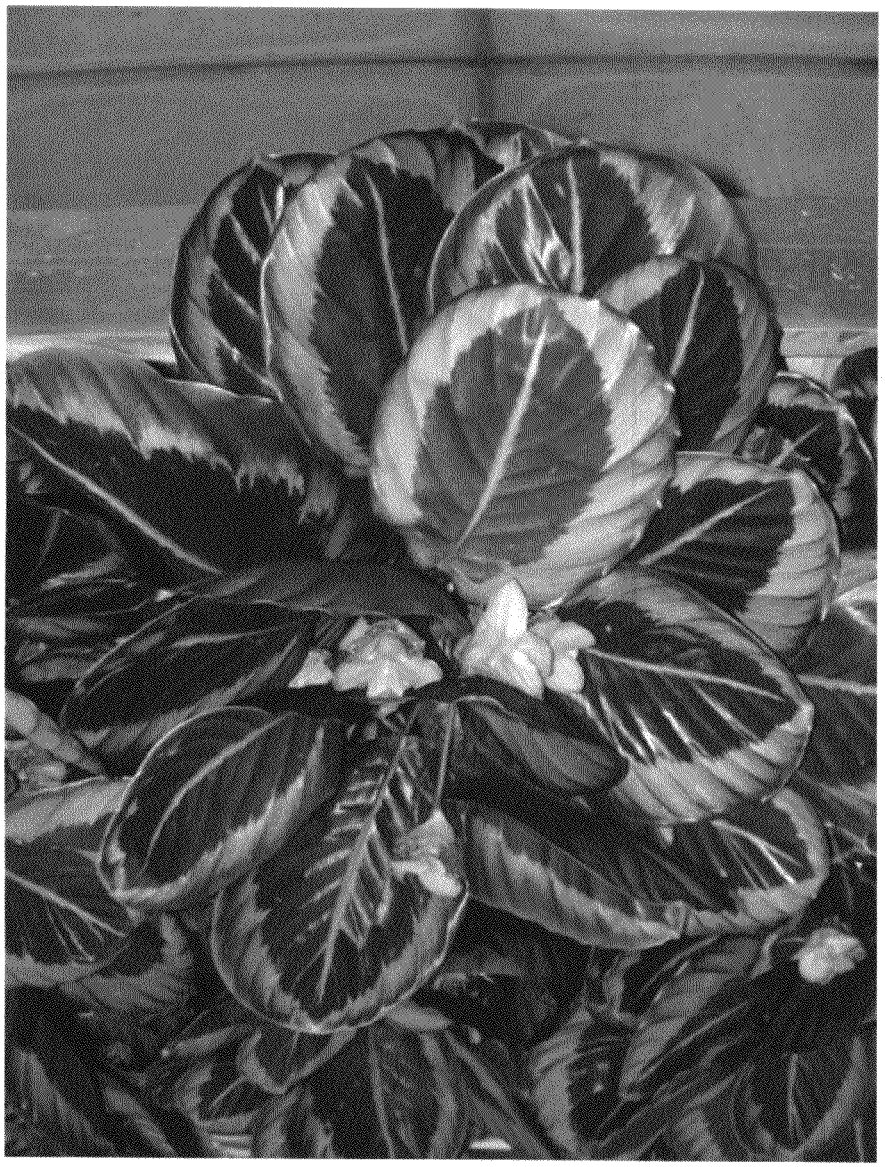
FIG. 1 is a photograph of an entire plant of the new variety.
Figure 2:
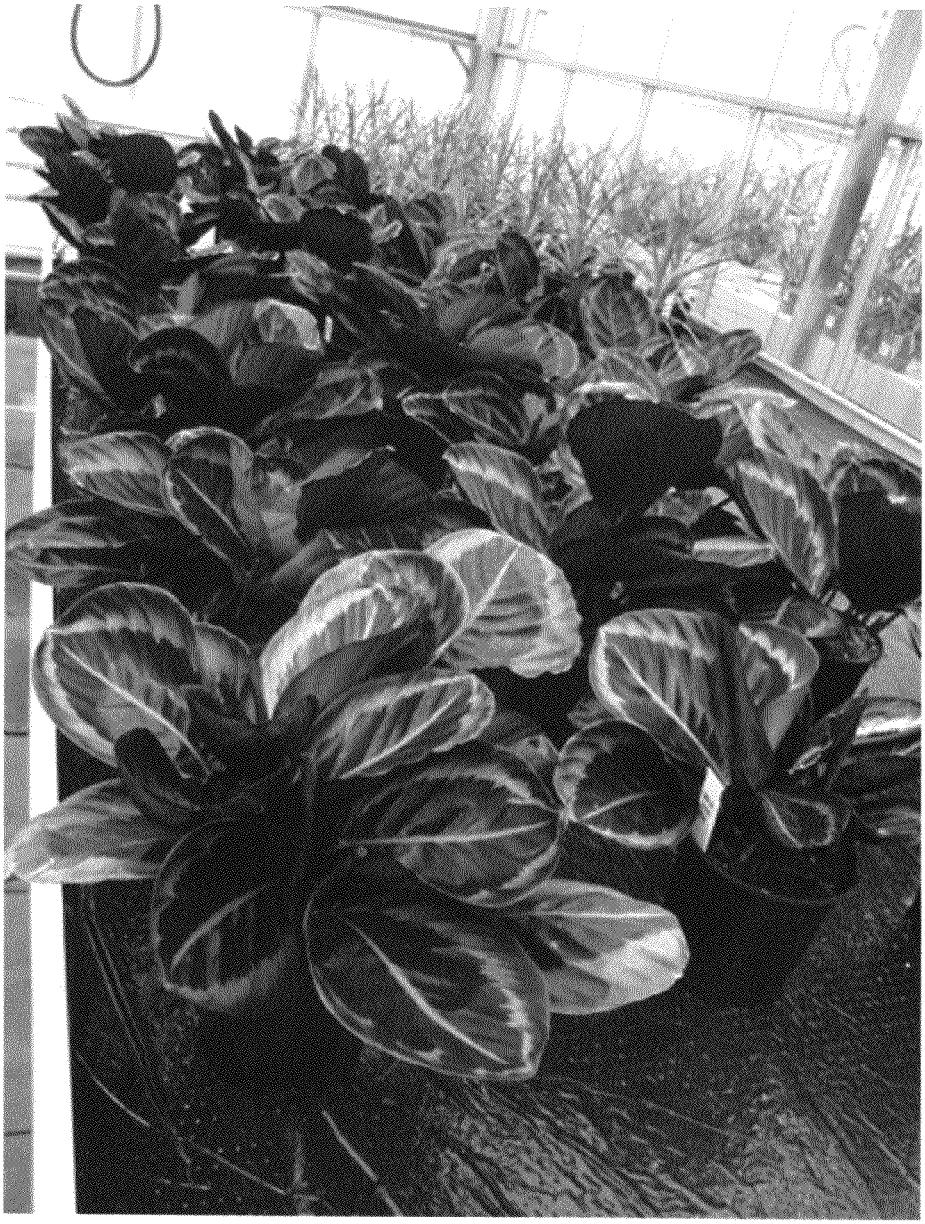
FIG. 2 is a photograph of multiple plants of the new variety.
Figure 3:
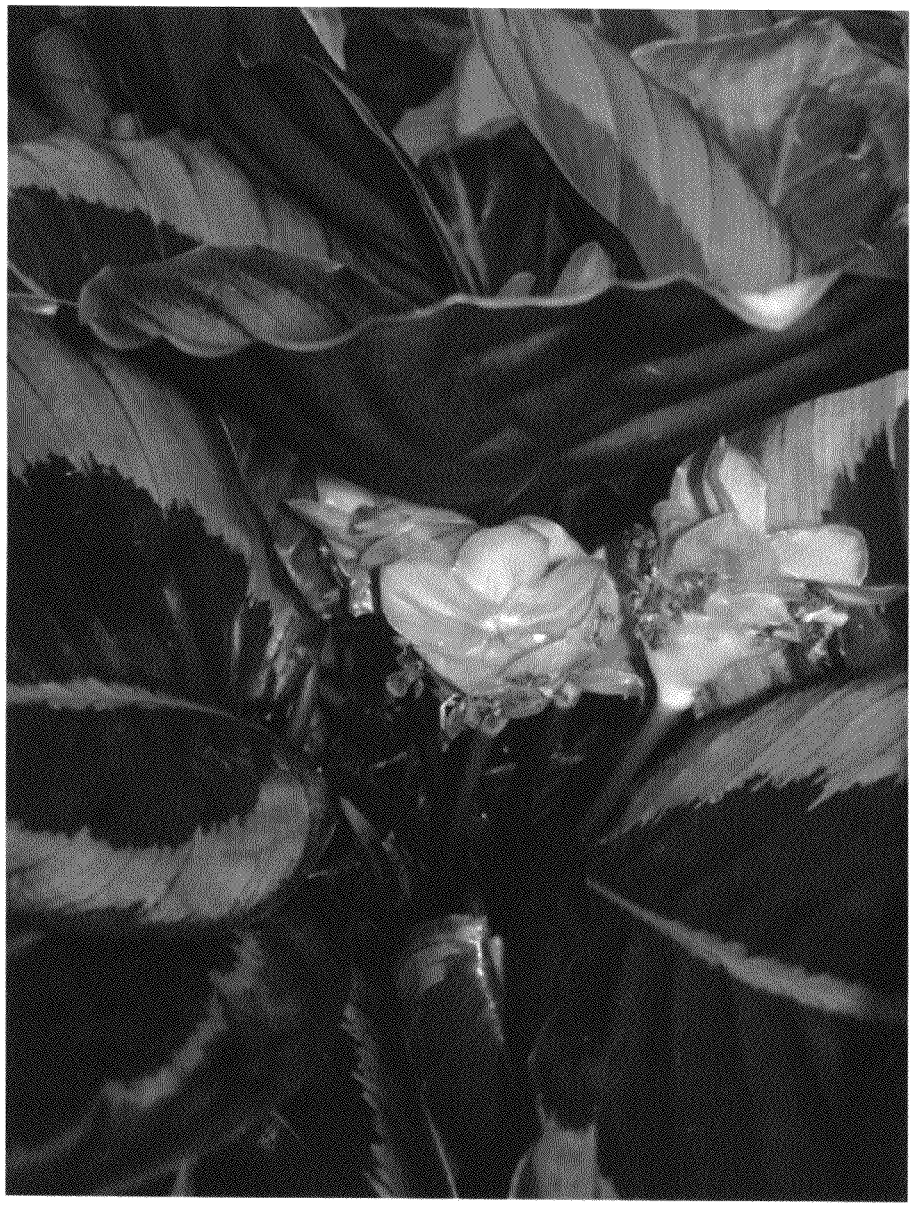
FIG. 3 is a close-up photograph of the new variety.
Figure 4:
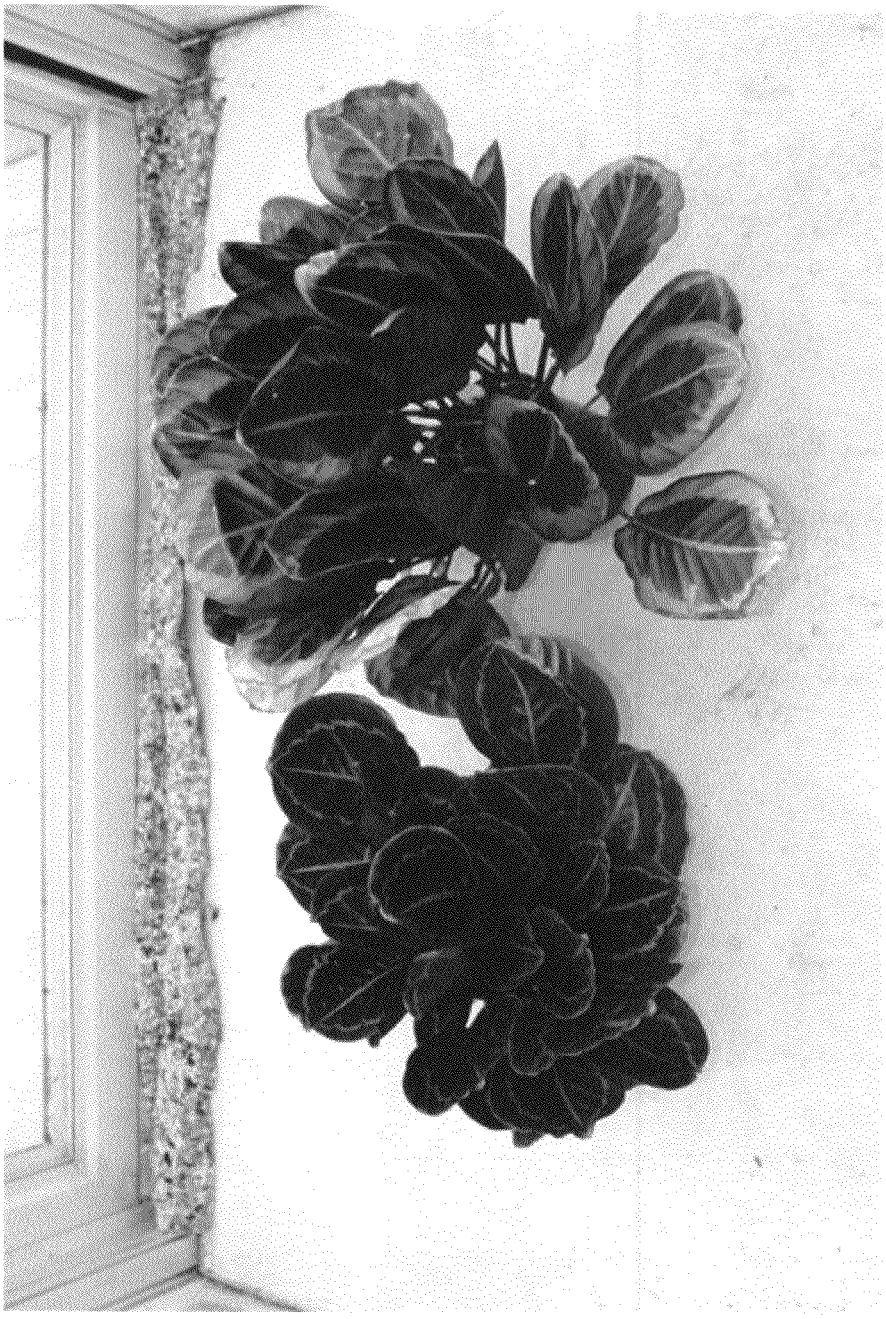
FIG. 4 is a comparison photograph of 'Dottie' (left) and 'Princess Jessie' (right).

'Princess Jessie' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 2001 Edition, except where general terms of ordinary dictionary significance are used. The plants were grown under natural light in Roelofarendsveen, The Netherlands. The plants were grown from tissue culture in 17 cm pots and were 24 days old when described. The temperature was from 19-23° C., and the relative humidity was 95%.

Propagation:

*Time to initiate roots.*—Summer: 7 days at 23° C. Winter: 7 days at 23° C.

*Time to produce a rooted cutting.*—Summer: 10 weeks. Winter: 12 weeks.

*Time to produce a finished plant from planting.*—36 to 40 weeks in a 17 cm pot.

The plant:

*Plant height from soil to top of plant plane.*—25-27 cm.

*Plant width.*—30-35 cm.

*Growth rate.*—36-40 weeks from a tissue culture plant to a sellable potted plant.

*Stem.*—Average number: 1, up to 6. Length: 8-10 cm. Diameter: 3-5 mm. Texture: Smooth. Color: 187A.

*Petiole.*—Length: 3-12 cm. Diameter: Upper part: 0.45-0.55 cm. Lower part: 0.6-0.8 cm. Texture: Smooth. Color: Approximately 187A, dark purple. Sheath: Length: Between 2-6 cm. Width: Between 0.3-0.7 cm. Apex: Nearly round at tip. Texture: Smooth. Color: Approximately 187A, dark purple. Geniculum: Length: Approximately 1 cm. Width: Approximately 0.5 cm. Texture: Smooth. Color: Approximately 187A, but a little less dark.

Leaves:

*Arrangement.*—Upside from each other.

*Number of leaves per lateral branch.*—3-4 leaves.

*Shape.*—Orbicular.

*Apex.*—Round.

*Base.*—Obtuse.

*Margin.*—Entire.

*Length.*—Between 10 and 16 cm.

*Width.*—Between 10 and 15.5 cm.

*Texture.*—Upper surface: Smooth and shiny. Lower surface: Smooth, with a dull sheen.

*Pubescence.*—None.

*Venation pattern.*—Primary veins on leaves radiate out from the midrib along the length of the leaf.

*Young leaf color.*—Upper surface: Approximately N189A. Lower surface: Approximately N186B.

*Mature leaf color.*—Upper surface: 202A. Lower surface: N186B.

*Vein color.*—Upper surface: 202A (mature leaves). Midrib: Between 186A and 186B. Lower surface: N186A.

Inflorescence description:

*Type/arrangement.*—Short, terminally bracted spike.

*Natural flowering season.*—Flower spikes appear after 40 weeks from tissue culture plants.

*Time to flower.*—About 6-8 weeks.

*Longevity.*—About one day per flower.

*Diameter.*—Approximately 3 cm.

*Depth.*—Approximately 3.5 cm.

*Rate of flower opening.*—Approximately 85%.

*Bud.*—Shape: Elongated and elliptic. Length: Approximately 2 cm. Diameter: Approximately 2.5 cm. Color: Between 144A and 144B.

*Terminal bracts.*—Number per inflorescence: Approximately 5-8. Texture: Smooth. Shape: Ovate. Apex: Obtuse. Base: Cuneate. Margin: Entire. Length: 2.6-2.9 cm. Width: 1.4-1.7 cm. Young bract color: Upper and lower surfaces: Between 147C and 148B. Mature bract color: Upper and lower surfaces: Between 147C and 148B; on the tip of the lower surface, there is a spot colored between 168A and 168B.

*Lower bracts.*—Number per inflorescence: 10-15. Texture: Smooth and shiny. Shape: Obovate. Apex: Obtuse. Base: Ovate. Margin: Entire. Length: 1.5-1.8 cm. Width: 2.0-2.5 cm. Young bract color: Upper and lower surfaces: 145D. Mature bract color: Upper and lower surfaces: 145D.

*Flowers* (*no commercial significance*).—Arrangement: Around the inflorescence. Number of flowers/buds per branch spike: 2-4. Number of flowers/buds per inflorescence: 10-15. Calyx: Number of sepals per flower: 3. Length: Approximately 1.6 cm. Width: Approximately 0.5 cm. Color: Approximately 145D. Sepal: Shape: Narrowly elliptic to linear. Length: Approximately 9-10 mm. Width: Approximately 3-4 mm. Apex: Acute. Margin: Entire. Corolla: Number of petals per flower: 3, parted. Length: Approximately 3 cm. Width: Approximately 0.5 cm. Color: Translucent; approximately 155D. Petal: Arrangement: Zygomorphic/irregular. Shape: Obviate. Length: 8-10 mm. Width: 3-4 mm. Apex: Acute. Margin: Entire. Base: Decurrent to obtuse. Texture: Smooth. Upper surface color: Between N81B and N82A. Lower surface color: Translucent; 155D. Staminoides: Number per flower: 3. Length: Two of them are about 3.5 cm, and the other one is about 3 cm. Width: Two of them are about 0.1 cm, and the other one is about 0.15 cm. Shape: Narrowly elliptic to linear. Color: 155D with 78C. Reproductive organs: Stamen number per flower: 1. Filament length: 2 cm. Anther length: 0.23-0.26 cm. Anther color: Approximately 155D. Pistil number per flower: 1. Pistil length: 2.3 cm. Stigma shape: Elliptic and cupped. Stigma color: Translucent; approximately 155D. Style length: 2.5-3 cm. Style color: Approximately 155D. Pollen amount and color: Not measured. Ovary length: 0.3 cm. Ovary color: 158B. Scapes: Length: 10-11 cm. Diameter: 0.35-0.4 cm. Strength: Strong. Texture: Smooth. Color: The base color is between 147C and 148B, and toward the upper part, the color is N186B.

General:

*Disease/pest resistance.*—Unknown.

*Temperature tolerance.*—Unknown.

I claim:

1. A new and distinct *Calathea roseopicta* (Linden) Regel plant named 'Princess Jessie' as is herein described and illustrated.

* * * * *